United States Patent [19]

Kurtz

[11] Patent Number: 4,531,004

[45] Date of Patent: Jul. 23, 1985

[54] DIMETRONIDAZOLE PHOSPHATES

[75] Inventor: Richard R. Kurtz, Portage, Mich.

[73] Assignee: The Upjohn Company, Kalamazoo, Mich.

[21] Appl. No.: 526,576

[22] Filed: Sep. 14, 1983

Related U.S. Application Data

[63] Continuation of Ser. No. 323,860, Nov. 23, 1981, abandoned.

[51] Int. Cl.$^3$ .............................................. C07F 9/65
[52] U.S. Cl. .................................. 548/112; 548/338
[58] Field of Search ........................................ 548/112

[56] References Cited

U.S. PATENT DOCUMENTS

| | | | |
|---|---|---|---|
| 2,944,061 | 7/1960 | Jacob et al. | 548/338 |
| 4,160,827 | 7/1979 | Cho et al. | 424/199 |
| 4,386,079 | 5/1983 | Lahti | 424/200 |

FOREIGN PATENT DOCUMENTS 873973 8/1979 Belgium .

OTHER PUBLICATIONS

Koransky, W. et al., CA, 52, 12609D (1962).
Finney, D. J., "Statistical Method in Biological Assay," Hafner Publication Co., New York, N.Y., 1952, pp. 524–530.
Miki, T. et al., "A Phosphorylation of Steroids and a Dienone-Phenol Rearrangement Leading to a Secosteroidal Aldehyde which has a Strong Toxicity" Chem. Pharm. Bull., vol. 22, No. 7, pp. 1439–1450 (1974).
Cremlyn, R. J. W. et al., "A Simple Phosphorylation Procedure for Cyclic Alcohols", Synthesis, pp. 648–650, (1971).
Lacey et al., "A Simple Synthesis of Choline Alkyl Phosphates", Tetrahedron Letters, vol. 21, pp. 2017–2020 (1980).
Postescu, I. D. et al., "Characterization of Metronidazole-Phosphate, A Water Soluble Metronidazole Derivatives, as a Radiosensitizer of Hypoxic Cells", Strahlentherapie, 155, pp. 358–361 (1979).
Hoffer, M. et al., "Synthesis and Antiprotozoal Activity of 1-(3-Chloro-2-Hydroxypropyl)-Substituted Nitroimidazoles", J. Medicinal Chemistry, vol. 17, No. 9, pp. 1019–1020 (1974).
Benazet, F. et al., "Chimiotherapie", C. R. Acad. Sc. Paris, 263, Serie D-pp. 609–611 (Aug. 8, 1966).

*Primary Examiner*—Richard L. Raymond
*Attorney, Agent, or Firm*—Sidney B. Williams, Jr.; Joan Thierstein

[57] ABSTRACT

This invention pertains to novel processes for preparing phosphorus derivatives of metronidazole. The invention is also particularly directed to the use of novel chloro containing phosphorus derivatives of metronidazole as intermediates in these processes. Furthermore, the intermediates are compounds which insofar as is presently known no one has previously prepared. Finally, the phosphorus derivatives of metronidazole prepared by the novel processes of the invention include novel analogs thereof.

2 Claims, No Drawings

DIMETRONIDAZOLE PHOSPHATES

DESCRIPTION

This is a continuation of U.S. application Ser. No. 323,860, filed Nov. 23, 1981, now abandoned.

SUMMARY OF THE INVENTION

This invention pertains to novel processes for preparing phosphorus derivatives of metronidazole. The invention is also particularly directed to the use of novel chloro containing phosphorus derivatives of metronidazole as intermediates in these processes. Furthermore, the intermediates are compounds which insofar as is presently known no one has previously prepared. Finally, the phosphorus derivatives of metronidazole prepared by the novel processes of the invention include novel analogs thereof.

BACKGROUND OF THE INVENTION

The compounds of formula $I_1$ include metronidazole phosphate and its salts which are disclosed in U.S. Pat. No. 4,160,827, which in turn are derivatives of the antibiotic compound metronidazole which is disclosed in U.S. Pat. No. 2,944,061. Furthermore, Belgian Pat. No. 873,973 which is equivalent to U.S. Pat. No. 4,160,827 discloses the use of pyrophosphoryl tetrachloride in a process which phosphorylates metronidazole. However, the process disclosed in the Belgian patent is distinguishable from that of the present invention. Particularly, the crystalline intermediates of the present invention have not previously been known. Therefore, it is now understood that the process conditions of the present invention are not appreciated in the prior art. Numerous advantages accrue from use of the invention process and novel intermediates therein such as purification of metronidazol phosphate and preparation of additional analogs not known in previous processes.

In general, phosphorylations of alcohols with phosphoryl trichloride and pyrophosphoryl tetrachloride are well known. Representative references of such phosphorylations include Koransky, W. et al., "Phosphorylation of Nucleosides with Pyrophosphoryl Chloride", Z. Naturforsch, 17, pp. 291-5 (1962), CA, 52, 12609D (1962); Miki, T. et al., "A Phosphorylation of Steroids and A Dienone-Phenol Rearrangement leading to a Secosteroidal Aldehyde Which Has a Strong Toxicity", Chem. Pharm. Bull., Vol. 22, No. 7, pp. 1439-50 (1974); Cremlyn, R. J. W. et al., "A Simple Phosphorylation Procedure for Cyclic Alcohols", Synthesis, pp. 648-50 (1971). Additionally, hydrolysis of phosphorus dichlorides are also known. For example, see Koransky et al. cited above, as well as, Lacey, et al., "A Simple Synthesis of Choline Alkyl Phosphates", Tetrahedron Letters, Vol. 21, pp. 2017-20 (1980). However, none of the above references teach the phosphorylation of metronidazole or the novel compounds of the present invention.

In addition to the disclosed usages in U.S. Pat. Nos. 2,944,061 and 4,160,827, the use of metronidazole and its analogs as an adjunct to radiation therapy in the treatment of cancer is disclosed by Postescu, I. D. et al., "Characterization of Metronidazole-Phosphate. A Water Soluble Metronidazole Derivative, as a Radio Sensitizer of Hypoxic Cells", Strahlentherapie, 155, pp. 358-61 (1979).

Further, background references teaching analogs of metronidazole and their uses are also found in Hoffer, M. et al., "Synthesis and Antiprotozoal Activity of 1-(3-Chloro-2-Hydroxypropyl)-Substituted Nitroimidazoles", J. Medicinal Chemistry, Vol. 17, No. 9, pp. 1019-20 (1974) and Benazet, F. et al., "Chimiotherapie", C. R. Acad. Sc. Paris, 263, Serie D-pp. 609-11 (8 Aug. 1966).

DETAILED DESCRIPTION OF THE INVENTION

The present invention includes novel compounds having the formula I, and pharmacologically acceptable salts thereof, wherein Y is hydrogen or alkyl of from 1 to 3 carbons, inclusive;

A is ethylene or $-CH_2CH(CH_2Cl)-$;

Q and $Q_1$ are the same or different and are $SR_3$, OR, chloro or $NR_1R_2$;

wherein

R is hydrogen, alkyl of from 1 to 6 carbons, aryl, arylalkyl or I(a) with the proviso that when one of Q or $Q_1$ is $NR_1R_2$ then the other cannot be $SR_3$, OR or chloro and both cannot be hydroxy;

wherein $R_1$, $R_2$, and $R_3$ are the same or different and are hydrogen or alkyl of from 1 through 6 carbons, aryl or aralkyl.

In the foregoing designation of the variables, alkyl of from 1 to 3 carbons means methyl, ethyl, propyl, or isopropyl.

Alkyl of from 1 through 6 carbons means methyl, ethyl, propyl, butyl, pentyl or hexyl and the isomeric forms thereof.

Aralkyl means benzyl, phenylethyl, phenylpropyl, phenylbutyl, phenylpentyl and isomeric forms thereof.

Metronidazole means compound II wherein Y is $CH_3$, and A is $-CH_2CH_2-$ or ethylene.

Another aspect of the present invention is a process (Scheme A) for preparing compounds having the formula I' wherein a compound having the formula II (wherein both Y and A of I' and II are as defined above) is contacted with a phosphorylating agent by a process having a temperature of $-78°$ C. to $+10°$ C., preferably no more than $-20°$ C. and a concentration of 0.1 moles/liter to 0.25 moles/liter of the formula II to solvent, and a molar ratio of compound II to the phosphorylating agent is from 0.8 to 1.0. Suitable phosphorylating agents include pyrophosphoryl tetrachloride, phosphoryl trichloride ($POCl_3$), dianilinophosphoro-chloridate, anilinophosphorodichloridate and di-t-butylphosphorochloridate as described in U.S. Pat. No. 3,487,068, incorporated herein by reference.

The compound I' can be partially hydrolyzed to obtain novel compound I" (Scheme B(a)). Further, I' and I" can be completely hydrolyzed to obtain the metronidazole phosphate and analogs shown as compound I''' (Scheme B(i) or (ii)) when ROH is HOH.

The compounds I' and I" are crystallized in the process for separation from the process mixture. Thus, an improved process to obtain compound I''' free from inorganic phosphates is provided. Particularly, the improved process is most preferred for the preparation of metronidazole phosphate shown as compound I''' wherein Y is $CH_3$, and A is $-CH_2CH_2$13.

A further surprising advantage of the present process results from the crystallization and separation of the novel compounds I' and I". These compounds I' and I" are now found to be useful for the further process to prepare the compounds of the invention within the definition of formula $I_1$. For example, it is well known that the OH groups on the phosphate moiety such as is found on compounds I" and I'" do not react with the reactants $HSR_3$, HOR and $HNR_1R_2$ of the present process. However, Cl (which means a chlorine substituent) of compounds I' and I" is readily replaced by the $-SR_3$, $-OR$ and $-NR_1$, $R_2$ moieties of the reactants. Thus the process is novel. Additionally, except for moieties $-OR$ wherein R is hydrogen, such replacement results in novel compounds which cannot be prepared from previously known compounds by known methods. Thus, the novel processes are for the preparation of compounds having the formula $I_1$;
wherein Y is hydrogen or alkyl of from 1 to 3 carbons, inclusive, A is ethylene or $-CH_2CH(CH_2Cl)-$;

T and $T_1$ are the same or different and are $SR_3$, OR or $NR_1R_2$; wherein

R is hydrogen, alkyl of from 1 through 6 carbons, aryl, aralkyl or I(a);

$R_1$, $R_2$, and $R_3$ are the same or different and are hydrogen, alkyl of from 1 through 6 carbons, aryl, or aralkyl, and with the proviso that when T or $T_1$ is $NR_1R_2$ then the other cannot be $SR_3$ or OR.

Generally, the above described process (Scheme A) for the preparation of compound I' is conducted in an inert solvent, preferably aprotic polar solvents such as acetone, tetrahydrofuran (THF), or acetonitrile.

The preferred solvent for use with pyrophosphoryl tetrachloride as the phosphorylating agent is either THF or acetonitrile and for use with phosphoryl trichloride as the phosphorylating agent the preferred solvent is THF. A slurry of compound II in the solvent (under a nitrogen atmosphere) is chilled to about $-78°$ C. to $+10°$ C., preferably no more than $-20°$ C., and most preferably $-40°$ C. to $-30°$ C. and the concentration of compound II in solvent is from 0.1 to 0.25 moles/liter, preferably about 0.22 moles/liter. Molar ratio of compound II to the phosphorylating agent is from 0.8 to 1.0. A phosphorylating agent such as phosphoryl trichloride or pyrophosphoryl tetrachloride is added over a period of about one hour. Criticality of the temperature and concentration ranges is related such that the metronidazole II dissolves before the desired metronidazole phosphate dichloride I' precipitates. The mixture is stirred until compound II is no longer present, as determined by thin layer chromatography (silica gel, 25 percent methanol, 75 percent aqueous sodium chloride visualized with UV light). Chilling is continued for several hours to allow all the heavy solids to settle. The supernatent liquid is separated and the residue is slurried with chilled (0° C. to $-30°$ C.) tetrahydrofuran, acetone or acetonitrile. These heavy solids are highly reactive intermediates. Therefore, although these solids are readily isolated, direct evidence of their structure by usual methods is not available. However, considering the starting materials, reactants and characterization of products obtained by conversion, particularly by reactions as shown in Scheme B, these heavy solids are identified as those corresponding to the compound I'.

Although the preparation of compound I wherein one of O or $Q_1$ is OR wherein R is I(a) can be accomplished by the above described process, a different process is preferred. In this process compound II is contacted with a phosphorylating agent in the presence of a tertiary amine. The preferred amine is pyridine. Generally, the process comprises stirring a mixture of compound II, the amine and the phosphorylating agent, preferably phosphoryl trichloride, in an inert solvent, preferably tetrahydrofuran, at from 10° C. to reflux, preferably from 20° to 30° C. The resulting intermediate is then reacted further, for example, hydrolyzed, in the same manner as described for compounds I' or I" infra.

Compound I' may be hydrolyzed to I" or I'". This hydrolysis may be accomplished by either adding water to the compound I' or by adding water to a slurry of compound I' in a solvent selected from among those named above. During this hydrolysis operation an exothermic reaction occurs. Such an exothermic dissolution of the solids is followed by an appearance of a second precipitate or mixture. If the molar ratio of water to compound I' is from 1:1 to 25:1 and the temperature is maintained from $-20°$ C. to 0° C. the resulting compound is I", which is included in the formula $I_1$, as shown in Scheme B. Again, since compound I" is highly reactive its structure can be substantiated in a manner similar to that described above in ascertaining the structure of I'.

If the molar ratio of water added to compound I' is from 1:1 to 100:1 or greater and the temperature is raised to 10° C. to 50° C., preferably 18° C. to 40° C. then the known metronidazole phosphate and its analogs shown as compound I'" results.

Generally, compound I' and compound I" are contacted with reactants (b), (c), or (d) as shown in Scheme B and more particularly as represented by (i) or (ii) in Scheme B to obtain the additional compounds represented by compound $I_1$. The temperature of this reaction is about from $-20°$ C. to 80° C. in approximately a molar ratio of I' (Scheme B(i)) or I" (Scheme B(ii)) to reactant (b), (c) or (d) of from 1:1 to 1:50. The products are isolated by conventional means, such as filtration, evaporation, crystallization, or chromatography.

The reactants shown in Scheme B denoted as (b), (c) or (d) are well known in the art. Likewise, compound II and phosphorylating agents of the present invention are known. See the various references cited above.

The following examples provide a process within which one of skill in the art may recognize variations for the preparation of novel compounds I' and I" as well as I'". Additional processes are also shown by the examples for the preparation of the remaining novel compounds of $I_1$. Thus, the examples provide the preparation of various products having formula I', and I", the known metronidazole phosphate included in formula I'" and the additional novel compounds I (both I'" and I are included in $I_1$). These examples are indicative of the scope of this invention and are not to be construed as limiting. Those skilled in the art will promptly recognize the appropriate variations from the procedure for appropriate starting materials which correspond to those described in the examples.

The preferred process of this invention is for the preparation of the metronidazole phosphate compound having the formula I'" wherein Y is $-CH_3$ and A is $-CH_2CH_2-$.

EXAMPLE I

Preparation for Metronidazole Monophosphate I'"

(Wherein Y is $-CH_3$ and A is $-CH_2CH_2-$)

A slurry of 300 g (1.75M) of metronidazole in about 8 liters of tetrahydrofuran (under a nitrogen atmosphere) is chilled to about $-20°$ C. to $-30°$ C. and 275 ml (2.0M) of pyrophosphoryl tetrachloride is added over a period of about one hour. The mixture is stirred until metronidazole is no longer present, as determined by thin-layer chromatography (silica gel, 25 percent methanol, 75 percent aqueous sodium chloride, visualized with UV light). Chilling is continued for several hours to allow all the heavy solids to settle. The supernatant liquid is separated and the residue is slurried with about 5 liters of chilled ($-20°$ C. to $-30°$ C.) tetrahydrofuran or acetone or acetonitrile. Over the next few minutes 500 ml of water is added to dissolve the solids. During this operation an exothermic reaction occurs and a second precipitate forms; the temperature is maintained below 0° C. These solids (I″) are separated and washed with two 500 ml portions of tetrahydrofuran. The solids are again dissolved in one liter of water. The temperature is increased to about 40° C., and metronidazole phosphate (I‴ wherein Y is $-CH_3$, and A is $-CH_2CH_2-$) precipitates. After a few hours at ambient temperature and subsequent chilling to about 5° C. the solids are separated, washed thoroughly with two 500 ml portions of cold absolute ethanol and dried to constant weight under vacuum at 40° C. to 50° C.

Additional material may be isolated from the filtrate by concentration to 500 ml, followed by dilution with an equal volume of ethanol. The additional solids are washed with cold ethanol and dried as described above.

Some additional product may be salvaged from the organic (tetrahydrofuran, acetone or acetonitrile) filtrates. These filtrates are combined and diluted with an equal volume of hydrocarbon solvent such as hexane or heptane. An oily product appears; it is separated and heated for several hours at 50° C. to 60° C. in 2-3 volumes of water. The resulting solution is then concentrated to remove water; the last traces of water are removed by azeoptropic distillation with acetonitrile. The resulting oily material is leached with 2-3 volumes of acetonitrile, then stirred with 5-10 volumes of ethanol, seeded and allowed to crystallize. The overall yields range from 70 to 80 percent of metronidazole phosphate (I‴ wherein Y is $-CH_3$, and A is $-CH_2CH_2-$) characterized by analytical and spectroscopic methods.

EXAMPLE II

Preparation of Diethyl Metronidazole Monophosphate (I wherein Y is $-CH_3$, A is $-CH_2CH_2-$, and both of Q and $Q_1$ are $-OCH_2CH_3$)

Ten grams (58 millimoles) of metronidazole (II wherein Y is $-CH_3$; A is $-CH_2CH_2-$) is slurried with 250 ml dry tetrahydrofuran at room temperature for 15 minutes. The temperature is lowered to $-25°$ C. under nitrogen and 10 ml of pyrophosphoryl tetrachloride (67 millimole) is added over 10 minutes. After 30 minutes no starting material is left as determined by TLC. The mixture is cooled to $-50°$ C. for 15 minutes, stick filtered and the solids then suspended in 100 ml fresh tetrahydrofuran. Twenty-five ml ethanol is added to the cold suspension ($-20°$ C.) and the mixture is warmed to room temperature over about 1½ hours. The solution is achieved at a temperature of 5° C. The temperature is slowly increased to reflux and maintained for 2 hours, cooled to room temperature and concentrated to an oil. A 5 gram aliquot of the oil is dissolved in 50 ml of water and extracted with 20 ml portions of methylene dichloride ($CH_2Cl_2$) two times. The methylene dichloride remaining each time is washed with water then concentrated to an oil. Three grams of oil are collected. An NMR of the oil indicates an excess of ethanol. Further purification is necesary. The oil is placed on a 125 g silica gel column and eluted with one liter of methylene dichloride. No UV active material is observed so the solvent is changed to 5 percent ethanol/methylene chloride. Four fractions are collected having a UV active, one spot material. These fractions are combined and concentrated to 1.3 g of light green oil. The NMR of the oil is consistent with diethyl metronidazole monophosphate (I wherein Y is $-CH_3$, A is $-CH_2CH_2-$, and both Q and $Q_1$ are $-OCH_2CH_3$), as follows:

NMR ($CDCl_3$; TMS); $\delta 1.28$ (triplet, 6H);

$\delta 2.53$ (singlet, 3H); $\delta 4.02$ (quartet, 4H);

$\delta 4.34$ (multiplet, 2H); $\delta 4.61$ (multiplet, 2H); $\delta 7.97$ (singlet, 1H).

EXAMPLE III

Preparation of Ethyl Metronidazole Monophosphate Hydrochloride Salt (I wherein Y is $-CH_3$, A is $-CH_2CH_2-$ and one of Q and $Q_1$ is OH and the other is $-OCH_2CH_3$)

Thirty grams (175 millimoles) of metronidazole (II wherein Y is $-CH_3$; A is $-CH_2CH_2-$) is slurried in 800 ml dry tetrahydrofuran for 15 minutes, cooled to $-25°$ C. and 28 ml (200 millimoles) pyrophosphoryl tetrachloride is added. The mixture is stirred for 2 hours, becomes a solution and then a mixture again. The mixture is stick filtered and the residue slurried in 500 ml tetrahydrofuran. Fifty ml of water is added at $-20°$ C., the mixture becomes a solution and then a mixture again. The slurry is stirred for 1½ hours at $-5°$ C., filtered and washed with 300 ml of tetrahydrofuran. The solids are added to 500 ml ethanol and dissolved at about 60° C. After refluxing for 10 minutes the solution is stirred overnight at room temperature. Next morning the ethanol is removed under vacuum and the oil azeotroped with acetonitrile. The oil dissolves in acetonitrile but does not crystallize. After removing most of the acetonitrile, carbon tetrachloride is added to azeotrope off the acetonitrile so that NMR can be run. The oil becomes very thick so the mixture is cooled to about $-5°$ C. and crystallization of a white solid is observed. The solids are filtered and washed with carbon tetrachloride and dried in vacuo at 40° C. A yield of 32.4 g of ethyl metronidazole phosphate hydrochloride salt, (I wherein Y is $-CH_3$, A is $-CH_2CH_2-$ and one of Q and $Q_1$ is OH and the other is $-OCH_2CH_3$), is obtained; m.p. 134.6° C.-137.5° C. The structure is confirmed by NMR.

Analysis Calculated: C, 30.48; H, 4.76; N, 13.33; P, 9.83. Found: C, 30.43; H, 4.84; N, 12.99; P, 10.13.

EXAMPLE IV

Metronidazole Chloromonophosphate (II″ wherein Y is $-CH_3$, A is $-CH_2CH_2-$, and one of Q and $Q_1$ is chloro and the other is $-OH$)

Thirty grams (175 millimoles) of metronidazole (II wherein Y is $-CH_3$, and A is $-CH_2CH_2-$) is slurried in 800 ml of tetrahydrofuran and cooled to $-30°$ C. under nitrogen. Twenty-five ml of pyrophosphoryl tetrachloride is introduced over 15 minutes. The white mixture is stirred for 1½ hours, stick filter and the residue slurried in 500 ml fresh tetrahydrofuran. Thirty ml of water is added and the temperature maintained between $-20°$ C. and 0° C. for one hour. The solids are filtered under nitrogen atmosphere and washed with 200 ml of tetrahydrofuran and dried for 15 minutes under a nitrogen atmosphere.

EXAMPLE V

The Hydrochloride Salt of Monomethyl Metronidazole Phosphate (the hydrochloride salt of I wherein Y is —CH$_3$, A is —CH$_2$CH$_2$—, and one of Q and Q$_1$ is OH and the other is —OCH$_3$)

About 20 g (65 millimoles) of the chloromonophosphate from Example IV above is added to 250 milliliters methanol and warmed slowly to reflux. The solution is achieved and the reaction is then heated to reflux for one hour. The mixture is retained overnight at room temperature. The next morning the solution is concentrated to a clear oil and diluted with carbon tetrachloride. Upon stirring at room temperature white solids precipitate. After stirring one hour at room temperature the solids are filtered and washed with 50 ml of carbon tetrachloride and dried to constant weight; 21.5 g of the hydrochloride salt of monomethyl metronidazole phosphate (I wherein Y is —CH$_3$; A is —CH$_2$CH$_3$; and one of Q and Q$_1$ is OH and the other is —OCH$_3$), described above is obtained having a melting point of 133.0° C.–135.0° C.

Analysis for C$_7$H$_{13}$N$_3$O$_6$ClP is for: Calculated for: C, 27.87 percent; H, 4.34 percent; N, 13.93 percent; P, 10.3 percent. Found: C, 27.90 percent; H, 4.50 percent; N, 13.95 percent; P, 9.55 percent.

EXAMPLE VI

The Hydrochloride Salt of Dimetronidazole Phosphate (the hydrochloride salt of I$_1$ wherein Y is —CH$_3$, A is —CH$_2$CH$_2$—, both of Q and Q$_1$ are I(a)

A slurry of 17 grams (g) (100 millimoles (mmole)) metronidazole, 7.8 milliliters (ml) (100 mmole) pyridine and 200 ml tetrahydrofuran (THF) is stirred under nitrogen at room temperature. A dropwise addition of 4.8 ml (50 mmole) phosphoryl trichloride over 10 min. creates a 10° C. increase in the reaction temperature. The mixture is stirred 48 hrs. at room temperature under nitrogen, and then treated with 15 ml H$_2$O. The mixture is refluxed for 2 hrs., then diluted with 50 ml H$_2$O. The THF is removed under vacuum and the H$_2$O is extracted with 30 ml portions of methylene chloride three times. The H$_2$O is azeotroped with enough acetonitrile to remove all the water. The resultant oil is dissolved in ethanol and diluted with THF until crystallization occurs. After several days at room temperature the mixture is filtered and the solids are washed with fresh THF then dried to constant weight to give 6.69 g (16.3% yield) of the dimetronidazole phosphate (I wherein Y is —CH$_3$, A is —CH$_2$CH$_2$, both Q and Q$_1$ are I(a)), hydrochloride salt.

Analytical Data: MP 145°–150° C. decomposition; Analysis for: C$_{12}$H$_{17}$N$_6$O$_8$P.HCL; Calculated for: C, 32.69%; H, 4.09%, N, 19.06%; P, 7.04%. Found: C, 32.33%, H, 4.17%, N, 18,43%; P, 7.77%.

Chemical derivatives of metronidazole as disclosed in the present invention may be separated as the compounds I$_1$ or as pharmacologically acceptable salts thereof. These can be acid addition salts, such as hydrogen chloride salts, or can be salts including cations, for example, H, Na, K, Li, one-half Ca, one-half Mg, one-third Al, one-half Fe, one-third Fe, NH$_4$, organic amines such as long chained primary amines, e.g., de- cyl-, lauryl-, myristyl-, palmityl-, or stearyl-amine, amines which yield crystal salts with organic acid, e.g., dicyclohexylamine, piperazine, benzylhydrylamine, amantadine, or tris(hydroxymethyl)aminomethane. Such cation containing salts can be readily prepared by known methods.

Starting with the novel compounds of the formula I pharmacologically acceptable salts may be prepared that are analogous to that described for metronidazole monophosphate of U.S. Pat. No. 4,160,827.

Those skilled in the art will recognize the appropriate variations from the procedures described herein both to the novel compounds having formula I, as well as the preparation of the pharmacologically acceptable salts thereof, for both reaction conditions and techniques.

Examples I through VI use a process for preparing compounds having formula I$_1$ through a novel intermediate I' prepared by the reaction as shown in Scheme A. Thus, preparation of analogous formula I$_1$ compounds can be accomplished by processes having variations within the ordinary skill in the art, including the preparation of corresponding novel intermediates I' shown in Scheme A. Further, as shown in Scheme B, analogous processes extend to the use of such I' intermediates to prepare like compounds of formula I''. Finally, therefore, it is understood that the Examples above are illustrative of the novel processes of this invention which may be varied to accomplish the reactions shown by Scheme A or Scheme B and described herein.

Particularly appropriate starting materials may be substituted in Example I for preparation of the corresponding novel intermediate I' according to the process described in Scheme A as shown by the following Table I.

TABLE I

I'

$$\begin{array}{c} \text{Y}-\overset{\displaystyle N\diagdown}{\underset{\displaystyle N}{\diagup}}-NO_2 \\ | \\ A-O-\overset{\displaystyle O}{\underset{\displaystyle |}{P}}-Cl \\ | \\ Cl \end{array}$$

| Y | A |
|---|---|
| —CH$_3$ | CH$_2$CH(CH$_2$Cl)— |
| —CH(CH$_3$)$_2$ | CH$_2$CH(CH$_2$Cl)— |

Further, appropriate intermediate I' may then be appropriately substituted in Scheme B to prepare a corresponding intermediate denoted as I'' as shown in Table II, as follows:

TABLE II

I''

$$\begin{array}{c} \text{Y}-\overset{\displaystyle N\diagdown}{\underset{\displaystyle N}{\diagup}}-NO_2 \\ | \\ A-O-\overset{\displaystyle O}{\underset{\displaystyle |}{P}}-Cl \\ | \\ OH \end{array}$$

| Y | A |
|---|---|
| —CH$_3$ | CH$_2$CH(CH$_2$Cl)— |
| —CH(CH$_3$)$_2$ | CH$_2$CH(CH$_2$Cl)— |

Finally, either I' or the latter compounds I" may be reacted as shown by the process in Scheme B to prepare novel compounds I as shown in Table III, as follows:

TABLE III $$\underset{\underset{Q_1}{|}}{\overset{\overset{O}{\uparrow}}{A-O-P-Q}}\text{-attached to N of } Y\text{-}\underset{N}{\diagdown}\text{-}NO_2 \text{ ring} \qquad I$$

| Y | A | Q | Q₁ |
|---|---|---|---|
| —CH₃ | —CH₂CH₂— | —N(CH₃)₂ | —N(CH₃)₂ |
| —CH(CH₃)₂ | —CH₂CH₂— | —N(CH₃)(C₂H₅)— | —N(CH₃)(C₂H₅) |
| —CH₃ | —CH₂CH₂— | —SCH₃ | —SCH₂CH₃ |
| —CH(CH₃)₂ | —CH₂CH₂— | —S—phenyl | —SCH₃ |
| —CH₃ | —CH₂CH₂— | —S—CH₂—phenyl | —SCH₃ |
| —CH(CH₃)₂ | —CH₂CH₂— | —S(CH₂)₅—CH₃ | —S(CH₂)₂CH₃ |
| —CH₃ | —CH₂CH₂— | —SH | —S(CH₂)₃CH₃ |
| —CH(CH₃)₂ | —CH₂CH₂— | —O—CH(CH₃)(CH₃) | —O—methyl |
| —CH(CH₃)₂ | —CH₂CH₂— | —OH | —O—phenyl |
| —CH₃ | —CH₂CH₂— | —O—CH(CH₃)(CH₃) | —O—ethyl |
| —CH(CH₃)₂ | —CH₂CH₂— | —O—methyl | —OH |
| —CH₃ | —CH₂CH(CH₂Cl)— | —OH | —O—ethyl |
| —CH(CH₃)₂ | —CH₂CH(CH₂Cl)— | —N(CH₃)₂ | —N(CH₃)₂ |
| —CH₃ | —CH₂CH(CH₂Cl)— | —N(CH₃)(C₂H₅) | —N(CH₃)(C₂H₅) |
| —CH(CH₃)₂ | —CH₂CH(CH₂Cl)— | —S—phenyl | —S—phenyl |
| —CH₃ | —CH₂CH(CH₂Cl)— | —S—isopropyl | —S—isopropyl |
| —CH(CH₃)₂ | —CH₂CH(CH₂Cl)— | —O—methyl | —OH |
| —CH₃ | —CH₂CH(CH₂Cl)— | —O—CH₂CH₂ | —OH |
| —CH(CH₃)₂ | —CH₂CH(CH₂Cl)— | —O—CH₂CH₂ | —O—ethyl |
| —CH₃ | —CH₂CH(CH₂Cl)— | —O—phenyl | —O—phenyl |
| —CH(CH₃)₂ | —CH₂CH(CH₂Cl)— | —O—phenyl | —O—benzyl |
| —CH₃ | —CH₂CH(CH₂Cl)— | —O—CH(CH₃)(CH₃) | —OH |
| —CH(CH₃)₂ | —CH₂CH(CH₂Cl)— | —OCH₂CH(CH₃)CH₂ | —OH |

Generally, the utility of the compounds denoted as Formula I₁, including the novel analogs of metronidazole phosphate (I) of the present invention, is within the teachings of U.S. Pat. No. 4,160,827 and disclosed in references such as U.S. Pat. No. 2,944,061 and by Postescu, I. D., et al., Hoffer, M. et al., and Benazet, F. et al., all cited above.

However, the formulation of novel compounds I, except when Q or Q₁ is chloro, prepared by the processes in the present invention are taught or use conventional techniques for the oral utility as fully disclosed in the references cited above.

On the other hand, it is of course recognized that novel compounds of formula I' and I" are intermediates useful in the novel processes of the present invention.

Additionally, the compounds I₁ of the present invention are found to exhibit antidepressant activity in mammals, for example, humans. Such activity is shown by testing its antagonism of oxotremorine hypothermia. The present compounds are tested as follows:

Groups of four male CF1 mice (18–22 gm each) are injected i.p. with test compound prepared in 0.25% methylcellulose and placed in plastic cages (6"×11"×5"). Thirty minutes later, oxotremorine hydrochloride is injected s.c. at 1 mg/kg after which mice are placed in a refrigerator maintained at 19° C. A control group of mice injected with oxotremorine alone is similarly housed. Thirty minutes after the administration of oxotremorine, intraperitoneal temperature is taken using a thermistor probe. A compound is considered to have antagonized oxotremorine if the body temperature is more than 2 S.D. above the X body temperature of the parallel control group which received oxotremorine alone. Active compounds are retested using multiple dose levels at 0.3 log intervals. ED50s are calculated by the method of Spearman and Karber described by Finney, D. J., "Statistical Method in Biological Assay," Hafner Publication Co., New York, N.Y., 1952 (pp. 524–530).

The dimetronidazole phosphate of Example VI caused reversal of hypothermia caused by oxotremorine at a dose of less than 20 mg/kg; reversal at a dose of 40 mg/kg is considered significant.

As antidepressants these compounds I₁ and their pharmaceutically acceptable salts can be used in dosages of from 75 mg/day to 200 mg/day and preferably 100 mg/day in oral or rectal preparations and in dosages of from 50 mg/day and preferably 100 mg/day in parental preparations as described in the above U.S. Pat. No. 4,160,827 for the class of compounds including metronidazole phosphates and its analogs having antibacterial activity therein. The exact amounts to be given are dependent on the age, weight and condition of the patient to obtain the desired pharmacological effect.

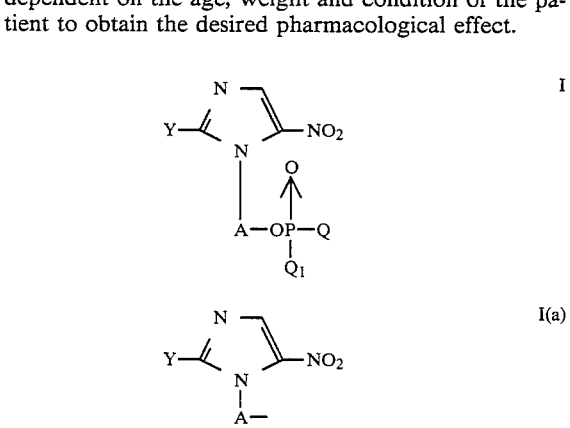

-continued
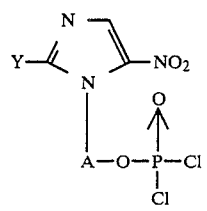
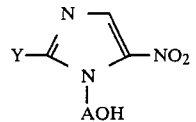
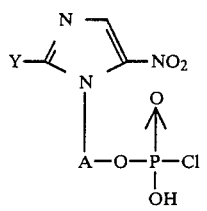
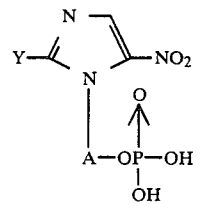
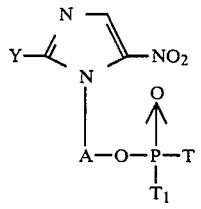
Scheme A
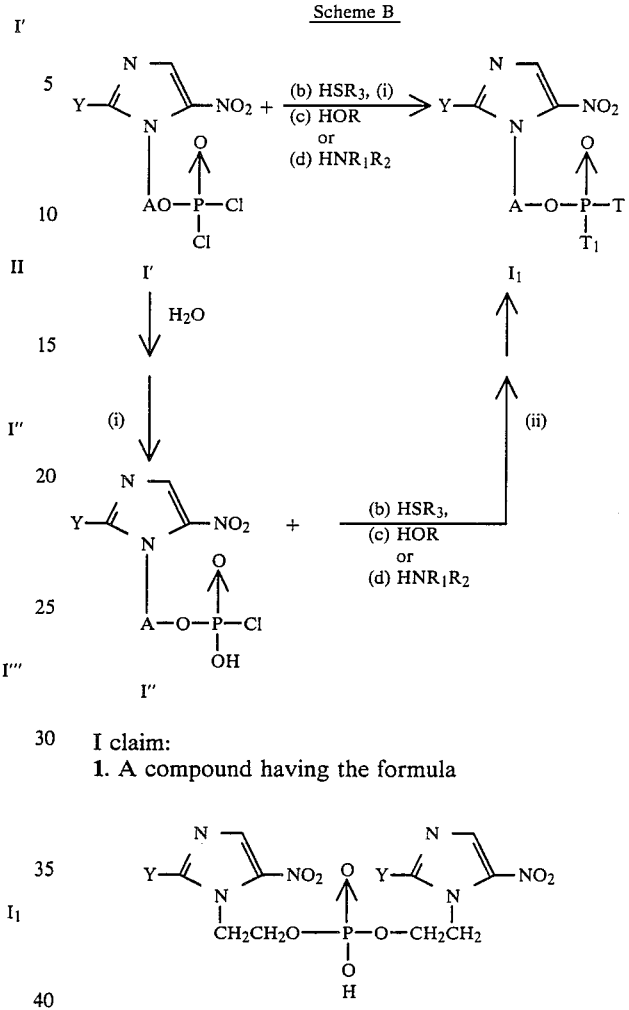
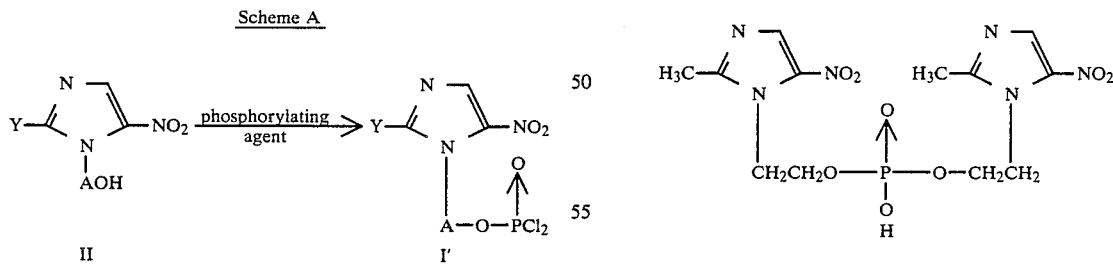
I claim:
1. A compound having the formula
wherein Y is hydrogen or alkyl of from 1 to 3 carbons inclusive.
2. A compound of claim 1 wherein Y is methyl so that the specific embodiment is a dimetronidazole phosphate having the formula
* * * * *

UNITED STATES PATENT OFFICE
CERTIFICATE OF CORRECTION

Patent No. 4,531,004                    Dated   July 23, 1985

Inventor(s)     Richard R. Kurtz

It is certified that error appears in the above-identified patent and that said Letters Patent are hereby corrected as shown below:

Column 2, line 65: "$CH_2CH_2$13." should read:  -- $CH_2CH_2$ --.

Signed and Sealed this

*Fifth* Day of *August 1986*

[SEAL]

*Attest:*

DONALD J. QUIGG

*Attesting Officer*  *Commissioner of Patents and Trademarks*